United States Patent [19]

Cabestany

[11] Patent Number: 4,959,061
[45] Date of Patent: Sep. 25, 1990

[54] HYDROPHILIC POLYMER BASED ON ACRYLIC ACID AND ALKALI METAL ACRYLATE, ITS METHOD OF PREPARATION AND ITS APPLICATION AS AN ABSORBENT, IN PARTICULAR OF A PHYSIOLOGICAL SOLUTION

[75] Inventor: Jean Cabestany, Stains, France

[73] Assignee: Societe Francaise Hoeschst, Puteau, France

[21] Appl. No.: 176,193

[22] Filed: Apr. 1, 1988

[30] Foreign Application Priority Data

Apr. 14, 1987 [FR] France ................... 87 05250

[51] Int. Cl.$^5$ ............................... A61F 13/16
[52] U.S. Cl. .......................... 604/368; 604/372
[58] Field of Search ..................... 604/368, 372

[56] References Cited

U.S. PATENT DOCUMENTS

| | | | |
|---|---|---|---|
| Re. 30,029 | 6/1979 | Smith | 604/372 |
| 3,669,103 | 6/1972 | Harper et al. | 604/372 |
| 4,074,004 | 2/1978 | Bateson et al. | 604/372 |
| 4,093,776 | 6/1978 | Aoki et al. | 526/240 |
| 4,104,214 | 8/1978 | Meierhoefer | 604/368 |
| 4,240,937 | 12/1980 | Allen | 604/368 |
| 4,270,977 | 6/1981 | Herman et al. | 604/372 |
| 4,286,082 | 8/1981 | Tsubakimoto et al. | 604/372 |
| 4,296,234 | 10/1981 | Mindt et al. | 604/368 |
| 4,486,489 | 12/1984 | George | 604/372 |
| 4,748,076 | 5/1988 | Saotome | 604/372 |

FOREIGN PATENT DOCUMENTS 2093351 9/1982 United Kingdom .

OTHER PUBLICATIONS

Chemical Abstracts. vol. 82, No. 10, 19 May 1975, p. 20, Columbus, Ohio.

*Primary Examiner*—C. Fred Rosenbaum
*Assistant Examiner*—Sharon Rose
*Attorney, Agent, or Firm*—Browdy and Neimark

[57] ABSTRACT

This polymer is based on acrylic acid and alkali metal acrylate; it has a degree of absorbency in respect of a physiological solution of 50 to 70 g/g, containing only 20 to 45% of acrylic acid, in molar proportions, and 80 to 55% of potassium acrylate. Its method of preparation is an oil-water suspension polymerization process which is carried out by introducing slowly, while being agitated, into the oil phase containing a protective colloid, a solution obtained starting from an aqueous solution of one or more polymerization initiators and an aqueous solution of the selected monomers, then eliminating any solvent until achieving a degree of dryness of 80±10% by weight, thus isolating the desired copolymer. This polymer is suitable for use as an absorbent.

10 Claims, No Drawings

HYDROPHILIC POLYMER BASED ON ACRYLIC ACID AND ALKALI METAL ACRYLATE, ITS METHOD OF PREPARATION AND ITS APPLICATION AS AN ABSORBENT, IN PARTICULAR OF A PHYSIOLOGICAL SOLUTION

FIELD OF THE INVENTION

The present invention relates to a hydrophilic polymer, its method of preparation and its application as an absorbent.

BACKGROUND OF THE INVENTION

Polymeric substances are known which are capable of absorbing several times their own weight of water, whereupon they are transformed into gel. These hydrophilic polymers are either natural or semi-synthetic polymers, such as derivatives of cellulose, starch, alginate, polysaccharides, or synthetic polymers based, in particular, on maleic acid or (meth)acrylic acid.

Therefore, a wide variety of hydrophilic polymers are known but for agricultural, horticultural or medical use it is still being endeavoured to find products which have a high absorption capacity not only for water but also for water charged with electrolytes, with a rapid absorption rate and satisfactory retention capacity in the state of a gel. Moreover, for hygienic applications, in particular in the production of articles intended to be brought into contact, while in a moist condition, with the human epidermis, it is endeavoured to find atoxic products which are inexpensive, which are not subject to syneresis and which contain neither nitrogenous derivatives nor residual monomers. It is fact that at present none of these known hydrophilic polymers meets the particular market requirements.

SUMMARY

The Applicant has surprisingly discovered a product of this type.

SUMMARY OF THE INVENTION

Therefore, the present invention relates to a hydrophilic polymer, in the form of microbeads, which is insoluble in water and based on acrylic acid and alkali metal acrylate, and which has a high degree of absorbency in respect of a saline physiological solution, of the order of 50 to 70 g per gram, characterized in that, to the exclusion of any other monomer, it is solely composed of an acrylic acid—potassium acrylate copolymer, containing a molar proportion of 55% to 80% of potassium acrylate.

DETAILED DESCRIPTION OF THE INVENTION

The copolymers defined above include, in particular, acrylic acid—potassium acrylate copolymers, containing molar proportions of 60% to 70% of potassium acrylate, e.g. acrylic acid—potassium acrylate copolymers in molar proportions of 35:65.

The expression saline physiological solution means an isotonic solution containing 9 g of sodium chloride per liter of distilled water.

The expression "to the exclusion of any other monomer" signifies the absence, even in very small proportions, of any product which exhibits in its structure a chemical function capable of reacting with acrylic acid, potassium acrylate or acrylic acid—potassium acrylate copolymer.

According to the invention, the copolymers defined above can be prepared using an oil-water suspension polymerization process which is carried out in an inert atmosphere, characterized by (A) introducing slowly, while being agitated, into the completely deoxygenated oil phase maintained at boiling point and containing a protective colloid, a solution obtained extemporaneously as it is being introduced, this solution starting from (1) a deoxygenated aqueous solution containing one or more water-soluble polymerization initiators having a half-life at 80° C. which is longer than two hours and (2) an aqueous solution containing at a concentration of 60±5% by weight the monomers selected; (B) then, when the polymerization reaction has ended, eliminating the solvents by azeotropic distillation until a suspension is obtained having a degree of dryness of about 80±10% by weight; and finally isolating the desired copolymer by filtration.

The oil phase comprises a hydrocarbon such as cyclohexane.

The protective colloid is chosen from those currently used in this type of suspension polymerization (cf. Kirk-Othmer, Encyclopedia of Chemical Technology, 3rd edition, volume 1, page 400). Advantageously, a cellulose ether is chosen and, preferably, a cellulose ethylether having an ethoxy group content of from 48% to 49.5% (c.f Encyclopedia of Polymer Science and Engineering, 2nd edition, volume 3, page 254). The protective colloid is previously dissolved or dispersed in the oil phase.

The polymerization reaction is initiated by one or more water- soluble free radical initiators having a half-life at 80° C. which is longer than two hours. Initiators of this type are constituted in particular by certain mineral peroxides, such as sodium peroxodisulphate or certain azo compounds, such as dicyano-4,4' azopentanedioic-4,4' acid, or the initiators used are dissolved in water and then this solution is carefully deoxygenated.

The potassium acrylate is preferably obtained in aqueous solution, by direct salification of an aqueous solution of acrylic acid with potash.

This salification process is preferably carried out at a temperature of between 20° C. and 35° C. The monomers used are dissolved in water at a concentration of about 60±5% by weight.

The aqueous initiating solution and aqueous monomer solution are mixed extemporaneously, in an inert atmosphere, as they are introduced into the agitated oil phase, which is completely deoxygenated and maintained at boiling point by external heating, if necessary.

These solutions therefore only remain in contact for a few seconds before use and as they are introduced slowly into the boiling reaction medium. The time taken to effect introduction may vary according to the operating apparatus, but generally it is between one and two hours. When introduction has ended, the reaction medium is preferably maintained at boiling point and under agitation to complete the polymerization process.

During the polymerization reaction, the copolymers formed are mutually and spontaneously cross-linked to provide cross-linked polymers which are insoluble in water, have a strong hydrophilic action and with very low proportions of residual monomers, which are always less than 0.01% by weight.

The extent to which this cross-linking is promoted is determined by how low the degree of neutralization of the acrylic acid is, how high the polymerization temperature is and the length of the half-life of the initiator or initiators.

The copolymers of the present invention are thus thermally cross-linked and, accordingly, become insoluble in water and acquire hydrophilic properties.

Furthermore, the person skilled in the art knows that the molecular masses of the copolymers formed are correspondingly higher as the initial concentration of monomers in the aqueous phase is increased and as the concentration of initiator is decreased. However, the person skilled in the art has at his disposal a set of kinetic parameters for modifying according to requirements the properties of the desired copolymers. These properties, which are those of the networks of cross-linked polymers, are readily accessible through a series of simple tests which make it possible to modify, where necessary, the operating conditions with a view to attaining the desired result.

Therefore, the absorbency of the polymer in respect of water is determined at 20° C., by agitating for 30 minutes 0.4 g of polymer in 500 g of water, then weighing the drained polymer gel obtained. The weight measured is corrected to 1 g of polymer. In this test the copolymers of the present invention are found to have an absorption capacity of the order of from 500 to 800 g per gram.

The absorbency of the polymer for the saline physiological solution is determined at 20° C., by agitating for 30 minutes 2 g of polymer in 500 g of saline physiological solution and then weighing the resultant drained polymer gel. The weight found is corrected, as previously, to 1 g of polymer. In this test the copolymers of the present invention are found to have an absorption capacity of the order of from 50 to 70 g per gram.

The rate of absorption of the saline physiological solution by the polymer is determined at 20° C. in a 100 ml beaker, the diameter of which is 55 mm and the height 70 mm, by agitating at a speed of 600 revolutions per minute with a magnetic agitator provided with a magnetized bar of 25 mm in length, 2 g of polymer in 50 g of saline physiological solution and measuring the time taken for the vortex to disappear. In this test the copolymers of the present invention require between 30 and 60 seconds for the vortex to disappear.

The proportion of extractable matter is determined in accordance with the following method:
1 g of the polymer to be tested is introduced into 200 g of saline physiological solution;
this suspension is agitated for 1 hour at 20° C., then left to stand for 15 hours at 20° C.;
the polymer gel obtained is drained and the filtrate, is collected;
the carboxylic and carboxylate functions present are determined on 100 cm3 of the filtrate;
the result of this determination is expressed in grams of polymer dissolved per 100 g of dry polymer.

In this test the copolymers of the present invention are present in a proportion of extractable matter of 5%-15%. At the end of the polymerization reaction, the reactive solvents are eliminated by azeotropic distillation until a suspension is obtained having a degree of dryness of 80 ±10%, then the suspension is filtered and the precipitate collected is dried to 90%-95% dryness.

The copolymers according to the present invention are thus isolated in form of beads with a diameter of several tenths of a millimetre, free of fines.

Therefore, the copolymers of the present invention possess significant absorption properties which justify their use as an absorbent and the invention also concerns, in the form of absorbents, the copolymers as defined in the foregoing, in particular for the manufacture of napkins or diapers for babies.

The following examples illustrate the invention without any restriction thereof.

EXAMPLE 1

In an inert atmosphere there are dispersed:
227.2 g of cellulose ethylether containing 48% to 49.5% of ethoxy groups and having at 25° C. a viscosity of 200 mPa.s in a 5% solution in a toluene-ethanol mixture, 80-20 by weight,
in 22723 g (270 moles) of cyclohexane.

A solution is introduced into this dispersion, which has been carefully deoxygenated, agitated and maintained at boiling point, over a period of 90 minutes in an inert atmosphere, said solution having been obtained by extemporaneously mixing as it is being introduced:
on the one hand, a deoxygenated solution of:
9.524 g (40 mmoles) of sodium peroxodisulphate dissolved in 144 g of water (8 moles);
on the other hand, a solution prepared extemporaneously by dissolving at a temperature below 30° C.:
7206 g (100 moles) of acrylic acid in
8759 g of an aqueous solution of potash containing 3647 g (65 moles) of potassium hydroxide and 5112 g of water (284 moles).

The resultant suspension is then maintained at boiling point for one hour while being agitated, it then undergoes azeotropic distillation until reaching a weight ratio of approximately 80% polymer and, finally, it is cooled to ambient temperature and filtered The precipitate is then dried to 90%-95% dryness under vacuum at 60° C.

In this way there are obtained 9675 g of an acrylic acid - potassium acrylate copolymer, 35-65 in molar proportions, which is insoluble in water and taking the form of beads of several tenths of a millimetre in diameter. This copolymer has a proportion of residual monomers of less than 0.005% by weight, an extraction rate of 12% by weight, an absorption capacity in respect of water of about 650 g per gram, an absorption capacity in respect of saline physiological solution of about 60 g per gram and a rate of absorption of saline physiological solution of 35 ±5 seconds.

EXAMPLE 2

In an inert atmosphere there are dispersed:
235.3 g of cellulose ethylether containing 48% to 49.5% of ethoxy groups and having at 25° C. a viscosity of 200 mPa.s in a 5% solution in a toluene-ethanol mixture, 80-20 by weight,
in 22807 g of cyclohexane.

A solution is introduced into this dispersion, which has been carefully deoxygenated, agitated and maintained at boiling point, over a period of 90 minutes in an inert atmosphere, said solution having been obtained by extemporaneously mixing as it is being introduced:
on the one hand, a deoxygenated aqueous solution of:
10.24 g (43 mmoles) of sodium peroxodisulphate dissolved in 144 g of water;
on the other hand, a solution prepared extemporaneously by dissolving at a temperature below 30° C.:
7206 g (100 moles) of acrylic acid in
8680 g of an aqueous solution of potash containing:
3928 g (70 moles) of potassium hydroxide and 4752 g (264 moles) of water.

The resultant suspension is then maintained at boiling point for one hour while being agitated, it then undergoes azeotropic distillation until reaching a weight ratio of approximately 80% polymer and, finally, it is cooled to ambient temperature and filtered. The precipitate collected is then dried to 90%-95% dryness under vacuum at 60° C.

In this way there are obtained 9865 g of an acrylic acid - potassium acrylate copolymer, 30-70 in molar proportions, which is insoluble in water and taking the form of beads of several tenths of a millimetre in diameter. This copolymer has a proportion of residual monomers of less than 0.005% by weight, an absorption capacity in respect of water of about 750 g per gram, an absorption capacity in respect of saline physiological solution of about 68 g per gram and a rate of absorption of saline physiological solution of 55 ±5 seconds.

It is to be understood that the present invention has only been described for illustrative purposes and without limitation, and that any modification, particularly insofar as equivalents are concerned, could be made thereto without departing from the scope thereof.

What is claimed is:

1. A cross-linked hydrophilic polymer which is insoluble in water which is based on acrylic acid and alkali metal acrylate, having a high degree of absorbency in respect of a saline physiological solution, of the order of 50 to 70 gr per gram, and which is solely composed of 20% to 45% of acrylic acid, in molar proportions, and 80% to 55% of potassium acrylate, in molar proportions, to the exclusion of any other monomer.

2. Hydrophilic polymer according to claim 1, which is an acrylic acid, potassium acrylate copolymer containing, in molar proportions, to 70% of potassium acrylate.

3. Hydrophilic polymer according to claim 1 in the form of beads.

4. An absorbent body of napkins or diapers for babies type containing a hydrophilic polymer, as defined in claim 1.

5. An absorbent body of napkins or diapers for babies type containing a hydrophilic polymer, as defined in claim 2.

6. An absorbent body of napkins or diapers for babies type containing a hydrophilic polymer, as defined in claim 3.

7. A polymer according to claim 1 in the form of an absorbent body.

8. A hydrophilic polymer according to claim 1 in the form of an absorbent body of beads.

9. A cross-linked hydrophilic polymer according to claim 1 having a water absorption capacity of between 500 and 800 grams per gram.

10. A cross-linked hydrophilic polymer according to claim 8 having a water absorption capacity of between 500 and 800 grams per gram.

* * * * *